United States Patent
Beran et al.

(10) Patent No.: US 11,583,639 B2
(45) Date of Patent: Feb. 21, 2023

(54) HEATING DEVICE FOR MEDICAL SOLUTIONS

(71) Applicant: Encompass Group, LLC, McDonough, GA (US)

(72) Inventors: Mark Beran, Neenah, WI (US); Jon Hermanson, Knoxville, TN (US)

(73) Assignee: Encompass Group, LLC, Atlanta, GA (US)

( * ) Notice: Subject to any disclaimer, the term of this patent is extended or adjusted under 35 U.S.C. 154(b) by 544 days.

(21) Appl. No.: 16/391,364

(22) Filed: Apr. 23, 2019

(65) Prior Publication Data

US 2020/0338279 A1    Oct. 29, 2020

(51) Int. Cl.
*A61M 5/44* (2006.01)

(52) U.S. Cl.
CPC ....... *A61M 5/44* (2013.01); *A61M 2205/0233* (2013.01); *A61M 2205/3368* (2013.01); *A61M 2205/36* (2013.01)

(58) Field of Classification Search
CPC ............ A61M 5/44; A61M 2005/2411; A61M 2205/36; A61M 2205/366
See application file for complete search history.

(56) References Cited

U.S. PATENT DOCUMENTS

| | | | |
|---|---|---|---|
| 2005/0148934 A1* | 7/2005 | Martens | A61M 5/445 604/113 |
| 2008/0077087 A1* | 3/2008 | Martens | A61M 5/44 604/113 |
| 2011/0194845 A1* | 8/2011 | Wang | F24H 1/142 392/468 |
| 2012/0063973 A1* | 3/2012 | Ang | A61J 1/10 422/555 |

* cited by examiner

*Primary Examiner* — William R Carpenter
(74) *Attorney, Agent, or Firm* — Baker Donelson Bearman Caldwell & Berkowitz PC

(57) ABSTRACT

There is disclosed a heating device which is adapted to be used to warm medical solutions contained within medical devices such as an intravenous bag, intravenous tube or respiratory circuit. The heating device includes an elongated flexible material tube having an interior medical solution channel and a pair of heat channels. The heat channels are filled or coated with a flexible, electrically conductive substance, which forms an electrical resistor. The conductive substance is electrically coupled to an electric power source controller. Electric current passing through the conductive substance creates heat which is transferred from the heat channels to the medical solution contained within the interior medical solution channel.

17 Claims, 1 Drawing Sheet

HEATING DEVICE FOR MEDICAL SOLUTIONS

TECHNICAL FIELD

This invention relates generally to heating devices, and more particularly to heating devices utilized to warm medical solutions contained within intravenous lines, intravenous bags, respiratory tubes, and the like.

BACKGROUND OF THE INVENTION

Intravenous solutions, fluids, blood, plasma, and other medications in liquid form, collectively referenced hereinafter as solutions, are typically administered to the patient to provide select fluids or medications directly into the patient's veins. These solutions are kept in IV bags to which an IV tube or line is coupled. The opposite end of the IV tube is fitted with an IV needle or catheter which punctures the patient's skin and enters the patient's vein.

A common problem with such IV solutions and blood is that they are usually stored at room temperature or refrigerated.

As such, their temperatures are far below the normal body temperature of a patient. The injection of these cool solutions into a patient may cause discomfort, or may even lower the body temperature of the patient to the point of causing hypothermia, which has been associated with increased infection rates, cardiac instability, coagulation complications and increased overall cost to the healthcare facility.

In order to avoid this problem, medical facilities may warm the solutions prior to administering to the patient. The contained solution may be warmed by placing it into a warming cabinet which raises the temperature of the solution. However, the rate of the administration can allow the solutions to cooled down within the IV line.

Other devices have been designed to warm the solution. One such device is a pair of warming plates between which the IV tube is positioned in a serpentine pattern to increase the contact area between the warming plates and the IV tube. A problem with this type of device is that the warming plate may cause hot spot in the IV tube causing the IV line to overheat the solutions, posing a risk to the patient.

Another device is in the form of a triple lumen tube wherein the IV line is surrounded by a circulating water jacket. Heat is exchanged between the warm water extending to the IV tube lumen in order to warm the IV solution passing through the IV tube. This type of device requires the circulation of heated water, which may cause entanglement of the lines or a spillage of the warming water.

A similar problem also exists with respiratory/anesthesia tubes or breathing circuits which provide air or gases to the patient. A breathing tube in a cool environment may create condensation within the tube or circuit during the breathing process, this may be referred to as "rain out". This condensation may interfere with the proper administration of air or gases to the patient, and thus should be avoided. For ease of explanation, these gases for medical purposes are also referenced herein as "solutions" or "fluids".

It would be beneficial to provide a device for warming IV solutions or respiratory gases to a patient which provides a safer and more consistent heat than those of the prior art. Accordingly, it is to the provision of such that the present invention is primarily directed.

SUMMARY OF THE INVENTION

In a preferred form of the invention a heating device for warming medical solutions comprises a flexible tube having a first end and a second end, the flexible tube having an medical solution channel extending between the first end and the second end. The flexible tube also having at least one heat channel containing an electrical resister in the form of a coating of electrically conductive, flexible substance.

DETAILED DESCRIPTION

Figure 1:
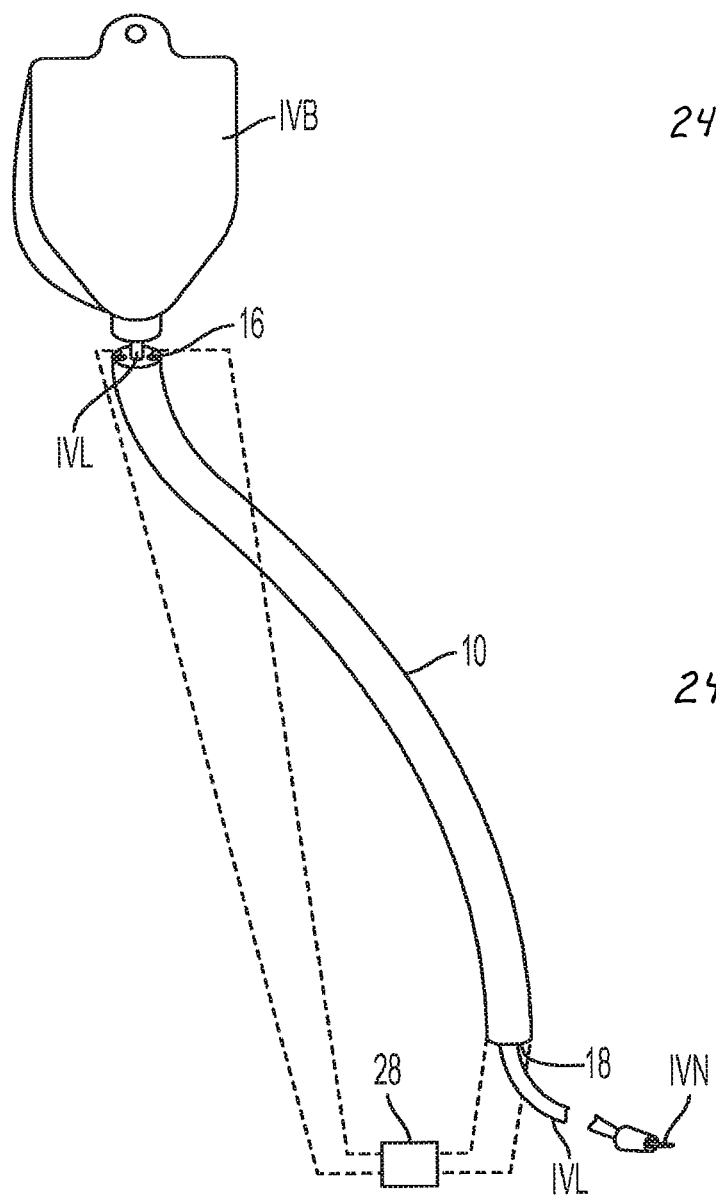
FIG. 1 is a perspective view of the heating device embodying principles of the invention in a preferred form.
Figure 2:
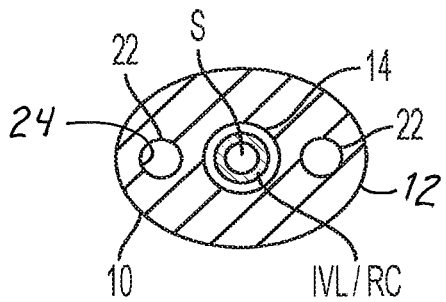
FIG. 2 is a perspective view of the heating device of FIG. 1.

With reference next to FIGS. 1 and 2, there is shown a warming device or heating device 10 which is adapted to be used to warm medical solutions contained within an intravenous tube or IV line IVL. As the warming device or heating device 10 is utilized in conjunction with other medical devices (IV line) containing a solution, it is referenced hereinafter as a heating device 10 for medical solutions. Alternatively, the heating device 10 may be used as the IV line itself. The heating device 10 is formed as an elongated flexible material tube or sleeve 12 having a generally central, interior IV line channel or medical solution channel 14 therein extending from a first end 16 to a second end 18. The first end 16 is positioned closely adjacent the connection between an IV solution bag IVB and the IV line IVL. The second end 18 is positioned adjacent the terminal end or coupler end to the IV needle IVN of the IV line IVL.

The flexible material tube 12 also has a pair of heat channels 22 extending between the first end 16 and the second end 18 on either side of the IV line channel 14. The heat channels 22 are filled or coated with a flexible, electrically conductive substance 24, such as a conductive ink of carbon, silver or other viscous conductive material which may then dry to form a circumferentially continuous and unbroken coating about the circumference of the heat channels 22, which forms an electrical resistor. The conductive substance 24 is electrically coupled to an electric power source controller 28.

In use, the IV line IVL is passed through the heating device IV line channel 14 so that the heating device 10 covers at least a majority of the IV line IVL.

With the heating device 10 activated, the electric power source controller 28 provides an electric current to the conductive substance 24 contained within the heat channels 22. The electric current causes the conductive substance 24 to increase in temperature, thereby causing heat to pass from the heat channels 22 to the IV line channel 14 positioned between or surrounded by the two heat channels 22. In turn, the heat passing to the IV line channel 14 heats the IV line IVL contained within the IV line channel 14. This heat warms the IV solution S contained within the IV line IVL prior to the solution entering the patient through the IV needle or catheter IVN coupled to the IV line IVL.

The quantity of heat produced by the heating device 10, or its temperature, is regulated through the controller 28. The quantity of heat may be tied to or regulated according to the flow or flow rate of the solution through the IV line IVL, i.e., the faster the fluid flows through the IV line the higher the temperature of the heating device 10 should be set to compensate for the shorter time the fluid passes through the heating device 10. This correlation between the flow rate of the solution and the flow of electric current from the controller 28 may be an automated program wherein the controller is in communication with the flow rate mechanism or controller of the IV solution, or may be manually controlled through a manual activation or desired temperature adjustment of the controller 28.

The heat transfer may also be controlled, or partially controlled, by the number of heat channels. While the invention may include a single heat channel, multiple heat channels is preferred to provide an even heat to the medical solution therein. As such, the number of heat channels may be any number, but is limited to the number of heat channels available within the limited space provided by the configuration of the sleeve or material tube 12.

Figure 3:
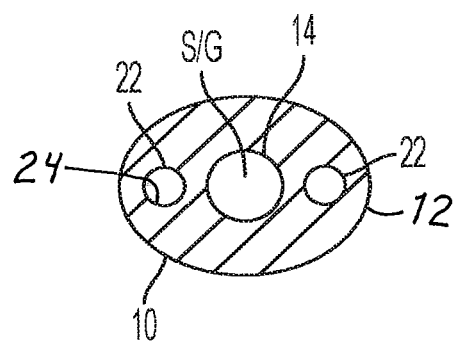
FIG. 3 is a perspective view of the heating device embodying principles of the invention in another preferred form.

With reference next to FIG. 3, there is shown a heating device 10 in another preferred form of the invention. Here, the heating device 10 is essentially the same as that previously described in reference to FIGS. 1 and 2 except that instead of the IV line IVL being positioned within the IV line channel 14, the IV solution S is carried within or transported directly within the IV channel 14. Hence, the heating device 10 is an IV line with heating capabilities.

In use, the heat produced by the electric current through the conductive substance 24 within the heat channels 22 is passed to the IV solution S flowing through the IV line channel 14.

It should be understood that a heating device 10 of the present invention in another form may be configured, as previously described, to surround, or at least partially surround, the IV bag IVB, alone or in addition to surrounding the IV line IVL. Thus, the medical solution channel 14 may surround or contain at least a portion of the IV bag IVB.

It should also be understood that the heating device 10 shown in FIGS. 1 and 2 may be configured to surround a respiratory tube or circuit RC, rather than an IV line. As such, the term medical solution line may be used herein to describe any line or tube which carries fluids therethrough, including but not limited to IV lines IVL and respiratory circuits RC. By surrounding the respiratory tube, the gases within the respiratory tube are warmed to prevent condensation within the respiratory tube. As such, it should be understood that the present heating device may be utilized with many different types of medical devices, including but not limited to medical tubes, lines, bags, or other devices to maintain them and the solutions (fluids, gases, liquids, etc.) flowing through them to the patient in a warm state.

Lastly, it should be understood that the heating device 10 shown in FIG. 3 may be configured to act as the respiratory tube or circuit itself. Therefore, the gases G for the patient travel through the central channel 14 without the addition of the respiratory circuit RC itself. The gases G are warmed by the current passing through conductive substance 24 and the heat produced therefrom, as previously described.

It thus is seen that a heating device for medical solutions is now provided which overcomes problems associated with heating device of the prior art. It should of course be understood that many modifications may be made to the specific preferred embodiment described herein, in addition to those specifically recited herein, without departure from the spirit and scope of the invention as set forth in the following claims.

The invention claimed is:

1. A heating device for warming medical solutions, comprising:
 a flexible tube having a first end and a second end, said flexible tube having a medical solution channel extending between said first end and said second end, said flexible tube also having at least two heat channels each containing an electrical resistor comprising a circumferentially continuous electrically conductive coating of electrically conductive, flexible substance.

2. The heating device of claim 1 wherein said medical solution channel is positioned between said at least two heating channels.

3. The heating device of claim 1 wherein said medical solution channel is sized and shaped to receive a separate and apart medical solution line therein.

4. The heating device of claim 1 further comprising an electrical controller electrically coupled to said electrical resistor.

5. The heating device of claim 4 wherein said electrical controller controls the electric current to said electrical resistor in accordance with the flow of a medical solution passing through said medical solution channel.

6. The heating device of claim 1 wherein said coating of electrically conductive, flexible substance is an electrically conductive ink.

7. A heating device for warming medical solutions contained within a medical solution line, comprising:
 a flexible sleeve having an elongated medical solution channel and at least two elongated heat channels extending parallel to said elongated solution channel, said elongated medical solution channel being sized and shaped to receive a separate and apart medical solution line therein, said at least two elongated heat channels each having a circumferentially continuous electrically conductive flexible coating substance therein.

8. The heating device of claim 7 wherein said medical solution channel is position positioned between said at least two heat channels.

9. The heating device of claim 7 further comprising an electrical controller electrically coupled to said electrically conductive flexible substance.

10. The heating device of claim 9 wherein said electrical controller controls the electric current to said electrically conductive flexible substance in accordance with the flow of a medical solution passing through said medical solution line.

11. The heating device of claim 7 wherein said electrically conductive flexible substance is an electrically conductive ink.

12. A heating device for warming medical solutions, comprising:
 a tubular sleeve having an elongated medical solution channel and a plurality of heat channels extending along a longitudinal length of said tubular sleeve, said plurality of heat channels having a resistive element therein formed of an electrically conductive flexible circumferentially continuous and unbroken coating substance therein.

13. The heating device of claim 12 wherein said plurality of heat channels surround said medical solution channel.

14. The heating device of claim 12 further comprising an electrical controller electrically coupled to said electrically conductive flexible substance.

15. The heating device of claim 14 wherein said electrical controller controls the electric current to said electrically conductive flexible substance in accordance with the flow of a medical solution passing through the elongated medical solution channel.

16. The heating device of claim 12 wherein said electrically conductive flexible substance is an electrically conductive ink.

17. The heating device of claim 12 wherein said elongated medical solution channel is sized and shaped to receive a separate and apart medical solution line therein.

\* \* \* \* \*